United States Patent
Esmailian et al.

(10) Patent No.: US 11,850,064 B2
(45) Date of Patent: Dec. 26, 2023

(54) SYSTEM FOR INTEGRATING DATA FOR CLINICAL DECISIONS INCLUDING MULTIPLE PERSONAL TRACKING DEVICES

(71) Applicant: IllumeSense Inc., Carlsbad, CA (US)

(72) Inventors: Markarit Esmailian, Encinitas, CA (US); Marcus Echols-Booth, Imperial Beach, CA (US); Muhammed Ibrahim Sezan, Carlsbad, CA (US); Adrian Hall, Los Angeles, CA (US)

(73) Assignee: Markarit Esmailian, Carlsbad, CA (US)

(*) Notice: Subject to any disclaimer, the term of this patent is extended or adjusted under 35 U.S.C. 154(b) by 186 days.

(21) Appl. No.: 17/125,691

(22) Filed: Dec. 17, 2020

(65) Prior Publication Data

US 2021/0186418 A1 Jun. 24, 2021

Related U.S. Application Data

(60) Provisional application No. 62/950,671, filed on Dec. 19, 2019.

(51) Int. Cl.
| | |
|---|---|
| *A61B 5/00* | (2006.01) |
| *G06N 20/00* | (2019.01) |
| *G16H 20/90* | (2018.01) |
| *A61B 5/0205* | (2006.01) |
| *G16H 40/67* | (2018.01) |

(52) U.S. Cl.
CPC .......... *A61B 5/4848* (2013.01); *A61B 5/0205* (2013.01); *A61B 5/7264* (2013.01); *G06N 20/00* (2019.01); *G16H 20/90* (2018.01); *G16H 40/67* (2018.01)

(58) Field of Classification Search
CPC . A61B 5/4848; A61B 5/0022; A61B 2505/07; A61B 5/0002; A61B 5/74; A61B 5/02; A61B 5/01; A61B 5/6801; A61B 5/7264; G16H 20/10; G16H 50/20; G16H 20/90; G16H 40/67; G16H 10/60;
(Continued)

(56) References Cited

U.S. PATENT DOCUMENTS

| | | | |
|---|---|---|---|
| 10,222,361 B2 | 3/2019 | Jackson, Jr. et al. | |
| 10,319,475 B1 | 6/2019 | Croan | |

(Continued)

OTHER PUBLICATIONS

T. Igarashi and J.F. Hughes. 2001. Voice as sound: using non-verbal voice input for interactive control. In Proceedings of the 14th annual ACM symposium on User interface software and technology (UIST '01). Association for Computing Machinery, New York, NY, USA, 155-156. https://doi.org/10.1145/5 (Year: 2001).*

(Continued)

*Primary Examiner* — Eric F Winakur
*Assistant Examiner* — Elina Sohyun Ahn
(74) *Attorney, Agent, or Firm* — Chernoff, Vilhauer, McClung & Stenzel, LLP

(57) ABSTRACT

An automatic system for making clinical decisions, especially with relation to cannabis use, that incorporates data from multiple personal tracking devices such as fitness trackers, analyzes that data using machine learning techniques to determine which data points are relevant to account for changes over time, and offers predictions, insights, and/or suggestions to support clinical decision making.

15 Claims, 9 Drawing Sheets

(58) Field of Classification Search
CPC ........ G16H 20/17; G16H 40/63; G16H 50/70; G06N 20/00; G06N 20/20
See application file for complete search history.

(56) References Cited

U.S. PATENT DOCUMENTS

| | | | |
|---|---|---|---|
| 10,799,660 B2* | 10/2020 | Klurfeld | A61M 11/00 |
| 11,069,446 B1* | 7/2021 | McNair | G16H 50/30 |
| 2001/0039503 A1 | 11/2001 | Chan | |
| 2004/0122702 A1 | 6/2004 | Sabol | |
| 2005/0074834 A1 | 4/2005 | Chaplen | |
| 2007/0077660 A1 | 4/2007 | Glas | |
| 2012/0271739 A1 | 10/2012 | Billingsley et al. | |
| 2013/0244238 A1 | 9/2013 | Neely | |
| 2016/0086021 A1 | 3/2016 | Grohman et al. | |
| 2016/0210332 A1 | 7/2016 | Milton | |
| 2016/0328991 A1 | 11/2016 | Simpson | |
| 2016/0337141 A1 | 11/2016 | Cameron | |
| 2017/0147769 A1 | 5/2017 | Bernstein | |
| 2017/0176255 A1 | 6/2017 | Nciri | |
| 2018/0060518 A1 | 3/2018 | Pappas et al. | |
| 2018/0279918 A1 | 10/2018 | Hagen | |
| 2018/0301211 A1* | 10/2018 | Pappas | A61B 5/163 |
| 2018/0357701 A1 | 12/2018 | Vu | |
| 2019/0027240 A1 | 1/2019 | Davidson | |
| 2019/0355472 A1 | 11/2019 | Kutzko | |
| 2019/0387796 A1* | 12/2019 | Cohen | A24F 40/30 |
| 2020/0118665 A1 | 4/2020 | Bender | |
| 2020/0199659 A1 | 6/2020 | Stoddard | |
| 2020/0202409 A1 | 6/2020 | Jikomes et al. | |
| 2020/0211688 A1 | 7/2020 | Liu | |
| 2020/0219167 A1 | 7/2020 | Jikomes et al. | |
| 2020/0305713 A1 | 10/2020 | Sipe | |
| 2020/0402662 A1 | 12/2020 | Esmailian et al. | |
| 2021/0158956 A1* | 5/2021 | Rodziewicz | G16H 20/90 |
| 2021/0193280 A1 | 6/2021 | Esmailian et al. | |
| 2021/0193281 A1 | 6/2021 | Smailian et al. | |
| 2021/0193282 A1 | 6/2021 | Esmailian et al. | |
| 2021/0193318 A1 | 6/2021 | Esmailian et al. | |
| 2022/0076830 A1 | 3/2022 | Cabigon et al. | |

OTHER PUBLICATIONS

U.S. Dept. of Health & Human Services. (Oct. 1, 2018,). ICD-10-CM official guidelines for coding and reporting FY 2019: Guidance portal. ICD-10-CM Official Guidelines for Coding and Reporting FY 2019 | Guidance Portal. from https://www.hhs.gov/guidance/document/icd-10-cm-o (Year: 2019).*

United States Patent and Trademark Office, International Search Report and Written Opinion dated Apr. 23, 2021 for International App. No. PCT/US2020/065697, 11 pages.

State Medical Board of Ohio, ICD-10 Required on Controlled Substance Prescriptions, May 2018, 4 pages, med.ohio.gov, Columbus, Ohio, USA. (https://www.med.ohio.gov/Portals/0/DNN/PDF-FOLDERS/Publications/E-News-NewsLetters/2018_05eNews.pdf).

United States Patent and Trademark Office, Final Office Action dated Jun. 22, 2022 for U.S. Appl. No. 16/903,144, 34 pages.

Alsherbiny et al., Medical Cannabis—Potential Drug Interactions, Dec. 2018, Medicines, 6(3) (Year: 2018).

Foster et al., Cannabis and Cannabinoids: Kinetics and Interactions, May 2019, The Am. J. of Medicine, 132(11), 1266-1270 (Year: 2019).

Sherimon, PC. Onto Diabetic: an ontology-based clinical decision support system for diabetic patients. Arabian Journal of Science and Engineering 41: 1145-1160. (Year: 2016).

Sansani, S. Development of knowledge-based system for personalized medicine by utilizing haplotype gene mapping. Procedia Technology 11: 1170-1180. (Year: 2013).

* cited by examiner

FIG7: TIME-BASED ARCHITECTURAL CHANGES (TBAC INTERACTION PATTERN)

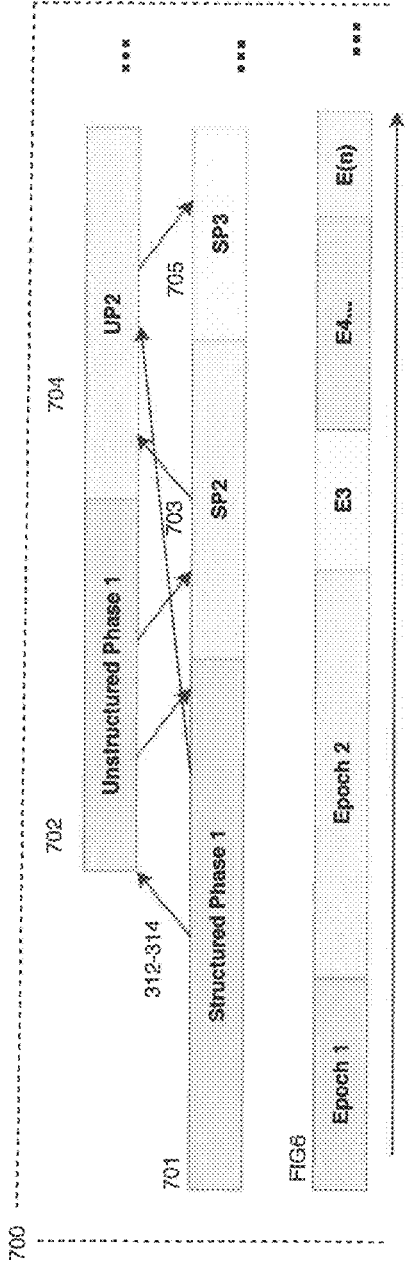

FIG6

1. The length of a UP or SP depends upon the state of the system represented in Figure 3 with respect to original members of the dataset from UP(n) or SP(n) for the lowest value of n still contributing at least one data point, i.e. length = time until 0 datapoints from either set UP(n) or SP(n) are in processing.
2. We define a subsequence as any part of the sequence from position x1 to x2 such that (x1 >= 1 & x2<=n) or (x1 > 1 & x2<=n).
3. The sequence will always start with one or more structured phases (SP).
4. Each subsequence also starts with one or more structured phases.
5. Each subsequence ends with exactly 1 unstructured phase (UP).
6. the data can pass through the UP(n) and SP(n) cycles by any path including a pattern of n SPs followed by 1 UP.
   E.g SP1, UP1, SP2, UP2, SP3, SP4, UP3, SP5, UP4.
7. The sequence will always end with the most recent structured phase SP(n).

Note: the lengths of SP(i) and UP(i) may differ from the length of the epochs E(n) (see FIG6) in that "phases" SP(n) and UP(n) represent generations of data structures storing results from algorithms running, whereas epochs represent generations of algorithm designs tuned according to results from machine learning.

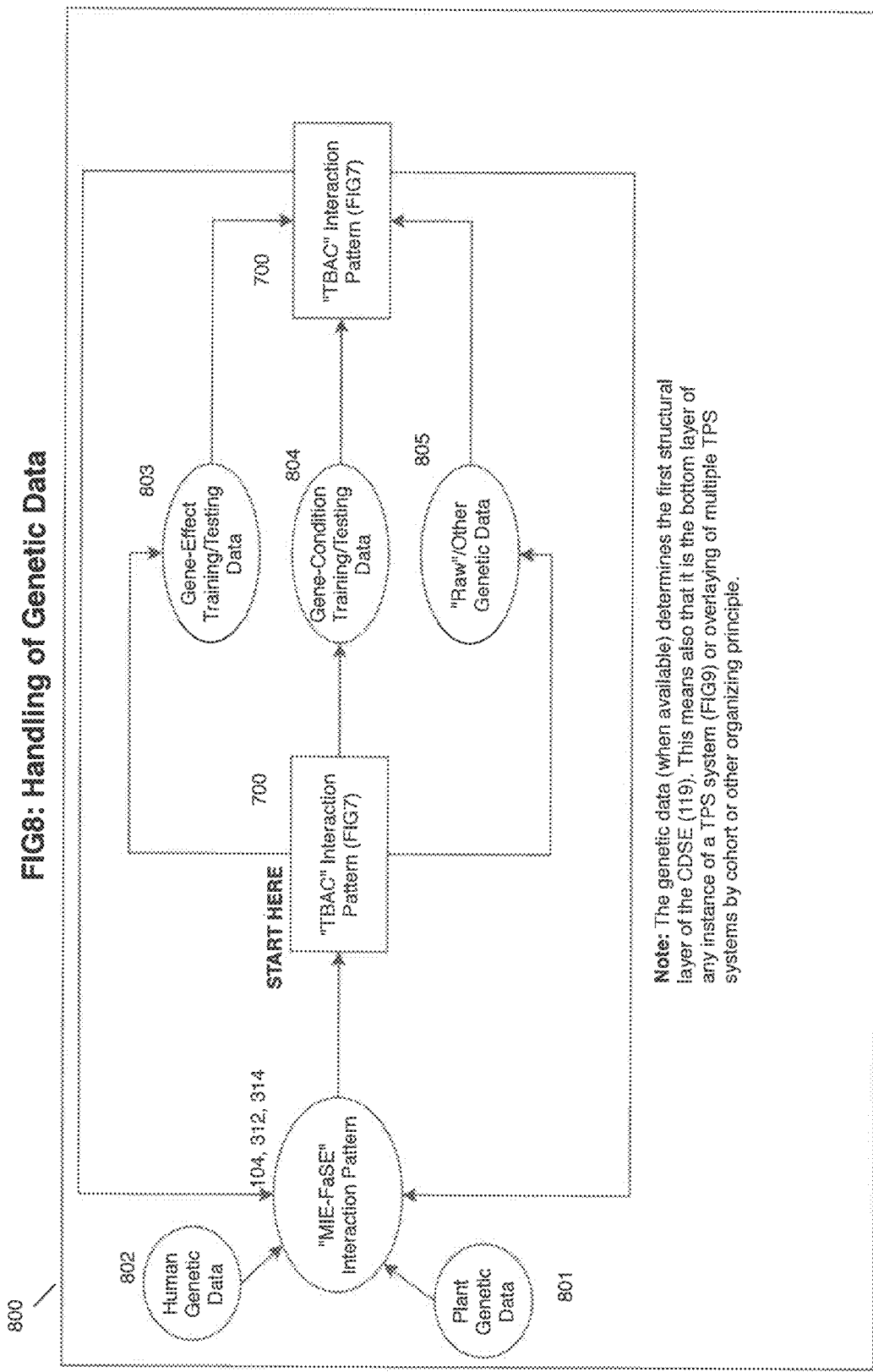

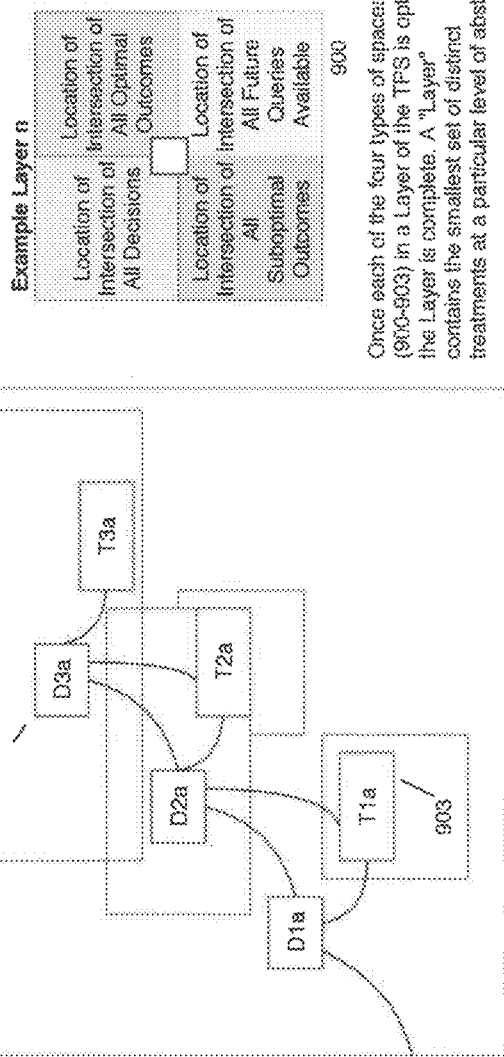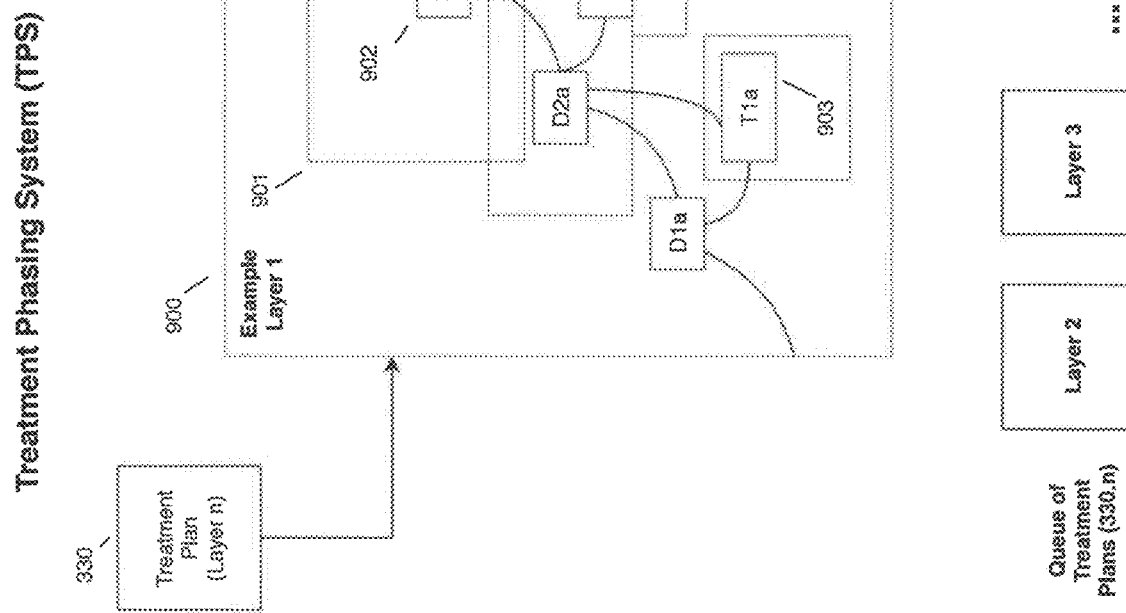
FIG. 9

SYSTEM FOR INTEGRATING DATA FOR CLINICAL DECISIONS INCLUDING MULTIPLE PERSONAL TRACKING DEVICES

CROSS-REFERENCE TO RELATED APPLICATIONS

This application claims the benefit of U.S. Provisional Patent Application No. 62/950,671 filed Dec. 19, 2019.

BACKGROUND OF THE INVENTION

Cannabis and cannabinoids have traditionally been used for various forms of medical treatment, such as analgesic and anticonvulsant effects. In more recent times, cannabis and cannabinoids have been used by cancer and AIDS patients who have reported relief from the effects of chemotherapy and wasting syndrome.

Cannabis and cannabinoids that are prescribed by physicians for their patients. Unfortunately, due to production and governmental restrictions, social stigma, and limited education, there has been limited clinical/scientific research into the safety and efficacy of using cannabis and cannabinoids to treat diseases. Evidence tends to indicate that cannabis may reduce nausea and vomiting during chemotherapy, may increase appetite in those with HIV/AIDS, and may reduce chronic pain and muscle spasms. Cannabis and cannabinoids may be administered through various techniques, such as capsules, lozenges, tinctures, dermal patches, oral or dermal sprays, cannabis edibles, vaporizing, smoking, etc.

Cannabis and cannabinoids also include some potentially adverse effects. The adverse effects may include tiredness, bloodshot eyes, depression, fast heartbeat, hallucinations, low blood pressure, dizziness, increased appetite, cardiovascular and psychoactive effects, memory impairment, impaired motor coordination, altered judgment, paranoia, etc.

A psychoactive cannabinoid found in cannabis and cannabinoids is tetrahydrocannabinol (or delta-9-tetrahydrocannabinol, commonly known as THC). Other cannabinoids include delta-8-tetrahydrocannabinol, cannabidiol (CBD), cannabinol (CBN), cannabicyclol (CBL), cannabichromene (CBC) and cannabigerol (CBG). Cannabis and cannabinoidscome in a multitude of strains, each of which has different chemical properties. Cannabis and cannabinoids are administrated typically by smoking it, inhaling it through a vaporizer, eating it, applying it topically to your skin, and placing liquid drops in the mouth.

Without meaningful clinical studies, it is problematic to meaningfully select an appropriate manner of administrating cannabis and cannabinoids, together with the selection of a particular strain of cannabis and cannabinoids. This selection may include a proper combination of the cannabinoids, the dose, the consumption technique, the frequency of consumption, and the times of its consumption.

The foregoing and other objectives, features, and advantages of the invention may be more readily understood upon consideration of the following detailed description of the invention, taken in conjunction with the accompanying drawings.

BRIEF DESCRIPTION OF THE SEVERAL VIEWS OF THE DRAWINGS

FIG. 7 illustrates time based architectural changes.
FIG. 8 illustrates handling of genetic data.
FIG. 9 illustrates treatment phasing system.

DETAILED DESCRIPTION OF PREFERRED EMBODIMENT

Figure 1:
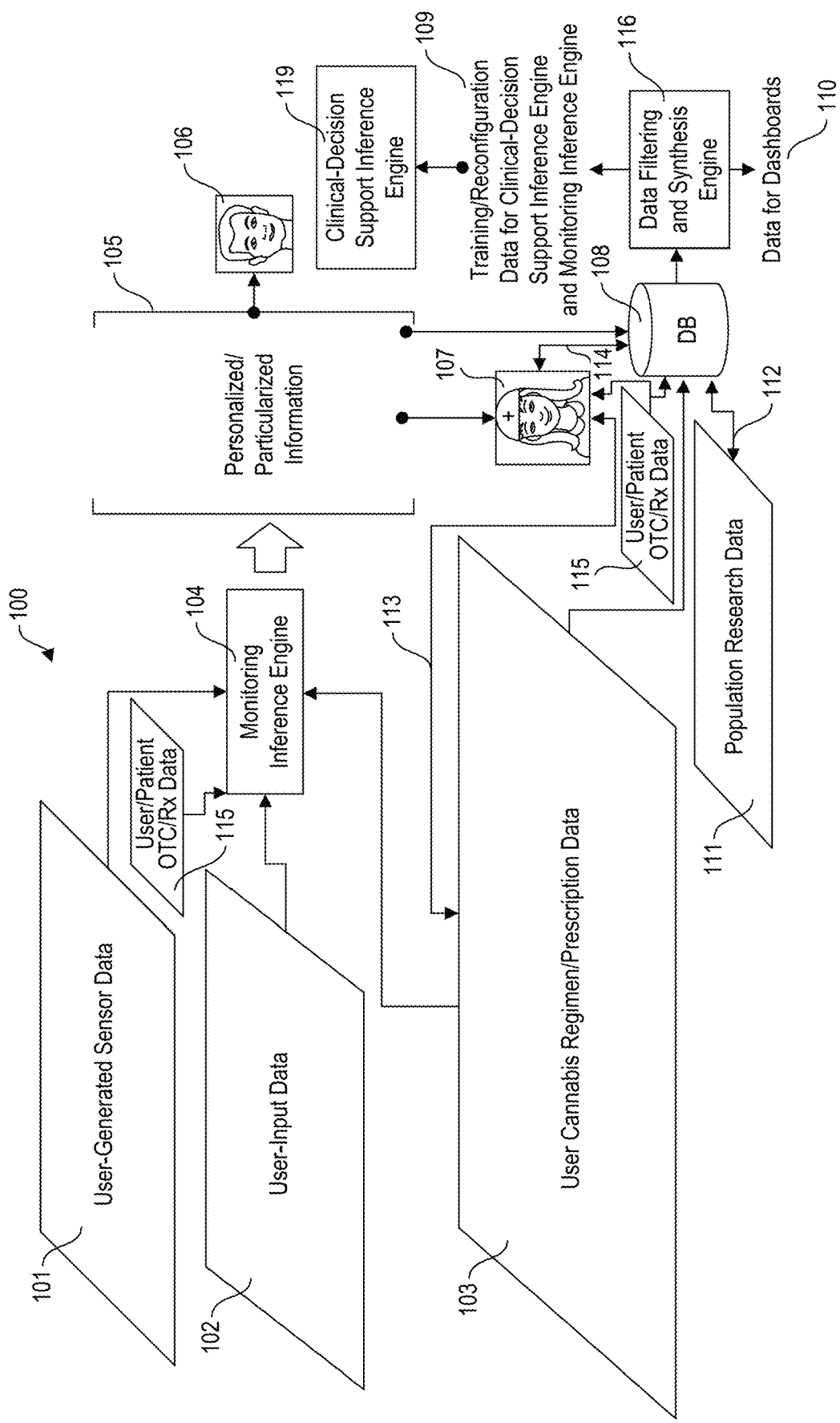
FIG. 1 illustrates a wellness system.

In addition to serving populations with medical needs, whose last resort may be a cannabis treatment, it is also desirable to provide cannabis and cannabinoids to a wellness conscious population who are reasonably healthy and use cannabis and cannabinoids both recreationally and to reduce minor annoyances, such as aches, pains, anxiety, and sleep problems. As a result of the desire, at least in part, to provide cannabis and cannabinoids to the wellness conscious population it is desirable to include personal wellness device(s) and software application(s) as part of the treatment landscape. To provide effective cannabis care, it is also desirable to leverage clinical data insights together with personal wellness device(s) in light of responsiveness to particular treatment regimens for particular patients and/or symptoms. In this manner, a potentially troublesome process of trial and error can be reduced. Moreover, the associated anxiety may also be reduced.

By way of example, Joe may be suffering from sleep problems. Joe finds himself awake in the early hours of the day and Joe often also has hard time falling asleep. Also, Joe frequently feels that his sleep is not so restful. In an attempt to determine the source of the sleep problems, Joe may use a personal wearable tracker device, which he often wears to bed, to monitor his sleep. The personal wearable tracker device may be watch or other device that includes an associated sensor. Further, Joe may also have a smart bed that he sleeps on, such as a SleepIQ bed, that also monitors his sleep. The smart bed is particularly useful when Joe does not want to wear his tracker to bed, or forgets to do so.

Joe sought cannabis treatment for his problem and was prescribed a regimen/prescription of a cannabis product he consumed in the form of a chocolate bar in the evenings. The detailed digital description of the product, including the chemical composition of the cannabis product specified by the manufacturer and the identity of the manufacturer, is available. After Joe starts with the regimen, Joe feels that there is some improvement in his condition. But Joe wants to confirm and quantify this improvement through the quantities that his personal devices track. Joe is also interested in even making further improvements with possibly refined/revised regimen/prescriptions. Joe inspects his tracker device, such as a Fitbit, and smart bed, such as a smart bed application, and tries to detect, quantify, and correlate the improvements with the specific changes in tracked quantities. The tracked quantities may include, for example, heart rate, time spent in light versus deep rem sleep, time awake, time to fall asleep, and restless versus restful sleep time. With the multitude of tracked quantities, Joe is quickly overwhelmed in his attempt to detect, quantify, and correlate the improvements. Further, with multiple different tracked quantities from multiple different personal tracking devices, Joe is even more quickly overwhelmed in his attempt to detect, quantify, and correlate the improvements. Moreover, detecting, quantifying, interpreting, and correlating changes over time is even more overwhelming.

To effectively detect, quantify, interpret, and correlate improvements a particularized wellness system is desirable. Referring to FIG. 1, a monitoring wellness system 100 may receive as an input user (e.g., patient) generated sensor data 101 from the patient. The user generated sensor data 101 from the patient may include data autonomously acquired through one or more tracking devices. The tracking devices may include wearables that include a sensor associated therewith, such as for example, smart watches, step trackers, GPS monitors, blood pressure monitors, and heart rate monitors, or personal devices that includes a sensor, such as for example, smart beds, or external devices embedded in the environment such as for example cameras and radar systems. Moreover, more than one tracking device may measure similar data, such as the number of steps taken during a day or other time period, and/or heart rate.

The monitoring wellness system 100 may receive as an input user input data 102 related to the patient. The user input data 102 related to the patient may include observational data that is provided, such as through a software application operating on a computing device which may be a mobile application on a mobile device. The observational data may include user input data, such as obtained as a result of surveys, of manual user input, or data acquired via "soft" sensors autonomously through interactions of the user with the mobile application or a smart speaker such as Amazon Alexa, which may include for example, information, such as emotions, autonomously inferred from analyzing pitch and volume of the patient's voice.

The monitoring wellness system 100 may receive as an input user CB regimen/prescription data 103 related to the patient. The user CB regimen/prescription data 103 may include a description of the cannabis product, such as brand, manufacturer's schema of the product including its chemical composition, etc. The user CB regimen/prescription data 103 may also include product administration and adherence information, such as dosage, timing, frequency, and form of delivery of the product. The administration and adherence data may be collected autonomously based upon smart connected delivery devices (e.g., mobile phone, or otherwise, or a wirelessly connected vaping device). The user CB regimen/prescription data 103 may also include medical classifications, such as ICD-10 and CPT code data, which may be provided by the patient's clinical care provider.

The monitoring wellness system 100 may receive as an input over the counter medication and prescription data 115 related to the patient. The over the counter medication and prescription data 115 may include a description of the over the counter and prescription, such as brand, manufacturer's schema of the product including its chemical composition, dosage, timing and frequency, and form of the delivery of the drug, etc. The system may further include particularized data for particular human DNA for certain gene variations of the patients of the system. For example, CYP450 tests provide information about how the body may respond to a particular drug. For example, CYP2C9 is a genetically polymorphic enzyme that is involved in the metabolism of warfarin, tolbutamide, losartan, torasemide, and many non-steroidal anti-inflammatory drugs, including diclofenac, ibuprofen, and flurbiprofen. Additional patient data 115 related to particular patients may include genomic data of the patient obtained from a genome sequencing. Specific genes, such as the Cytochrome P450 (CYP450) gene, and variations in these genes, i.e., polymorphisms, may cause significant differences in patient's ability to metabolize external substances, such as traditional medications and cannabinoids. Variations in CYP450 genes may affect the function of the enzymes produced by these genes, and thus affect the metabolization of various external molecules and chemicals introduced to the body. Such genomic data may be utilized by a Monitoring Inference Engine 104 and/or a Clinical-Decision Support Inference Engine 119 and/or a Data Filtering and Synthesis Engine 116 described later, in determining the appropriate dosage of the cannabis treatment and/or that of traditional-medication treatment.

The monitoring wellness system 100 may include a monitoring inference engine 104 which receives user generated sensor data 101, user input data 102, user CB regimen/prescription data 103, and/or patient over the counter medication/prescription data 115. The monitoring inference engine 104 may receive such data on a periodic basis, as such data is available. The monitoring inference engine 104 may include a machine learning based processing engine which may include artificial neural networks. The machine learning may include a deep learning architecture, such as deep neural networks, deep belief networks, recurrent neural networks, convolutional neural networks, generative adversarial network (e.g., two or more networks contest with one another), etc.

The monitoring inference engine 104 may infer specific changes in tracked quantities (e.g., measured by one or more devices), and some or all of those changes in tracked quantities may be attributable to a particular CB regimen/prescription. The patient may have multiple CB regimens being used at the same time, with each of them being dynamic and changing over time. The monitoring inference engine 104 may track each of the CB regimens in a separate manner from one another, or in a joint manner with each other.

The monitoring inference engine 104 may as a result of processing the available input data, present particularized/personalized information 105 to the patient 106. The particularized/personalized information 105 may be presented to the user in a suitable manner, such as a mobile application, rendering data on a display, operating on a mobile phone or in an expanded version of a native application of the patient's sensor device. The particularized/personalized information 105 may include specific changes in tracked quantities, which may be dependent on the particular CB regimen/prescription and the implications thereof. The particularized/personalized information 105 may also be provided to the patients' clinician/educator 107.

As previously described, the monitoring inference engine 104 may fuse data from multiple sensor based devices that provide user generated sensor data 101, which may be simultaneously sensing and measuring, where fusion refers to leveraging the redundancies and diversities in the data to determine increasingly accurate and complete inferences. The monitoring inference engine 104 also "fuses" the user-input data 102 with the user-generated sensor data 101, and "fuses" the user CB regimen/prescription data 103 with the user generated sensor data 101, and/or "fuses" the patient over the counter medication/prescription data 115 with the user generated sensor data 101. Also, by way of example, exploiting the redundancies between two sets of user generated sensor data 101 that have similar characteristics may be performed in a manner that results in a decrease in the noise and an increase in the confidence that the data is accurate. Also, by way of example, exploiting the diversities between two sets of user generated sensor data 101 that have different characteristics may be performed in a manner that results in a decrease in the noise and an increase in the confidence that the data is accurate.

As a result of processing data with the wellness system, the system may identify the particular sensor based devices, such as the wearable devices, for each particular user. With the accuracy of each type of wearable device being different, the system may select one of the identified wearable device data over the other identified wearable device data, both of which are available, to use as data for the monitoring inference engine 104.

In addition, data from the monitoring inference engine 104 may be provided to a patient's healthcare provider/team (e.g., clinician/educator) 107 through a suitable "clinician/educator" viewpoint (e.g., dashboard). In return, the patient's clinician/educator or healthcare provider team 107 may make changes to the patient's CB regimen/prescription, as depicted by bidirectional flow 113 in FIG. 1 between the user CB regimen/prescription data 103 and the patient's healthcare provider/team 107. The updated user CB regimen/prescription data 103 is then provided to the monitoring inference engine 104 for further processing.

Further, if desired, data from the monitoring inference engine 104 and/or the particularized/personalized information 105, including data derived from the output, of the monitoring inference engine 104 may be stored in a database (DB) 108 along with the user CB regimen/prescription data 103 and the information provided by the clinician/educator 107, which may include soap and patient progress notes. The soap note (which is an acronym for subjective, objective, assessment, and plan) is a documentation technique employed by health care providers to write out notes in a patient's chart, along with other common formats, such as an admission note. The DB 108 may also store patient's over the counter treatment medication (OTC) and patient's traditional prescription (Rx) data 115, and population research data 111. The population research data 111 may also include condition specific surveys and observational notes. The system may also consider other form of medical records, such as lab results, X-rays, cat scans, MRIs, ultrasounds, physician notes, diagnosis and treatment plans, to the extent they are made available by the patient and/or clinician.

Figure 2:
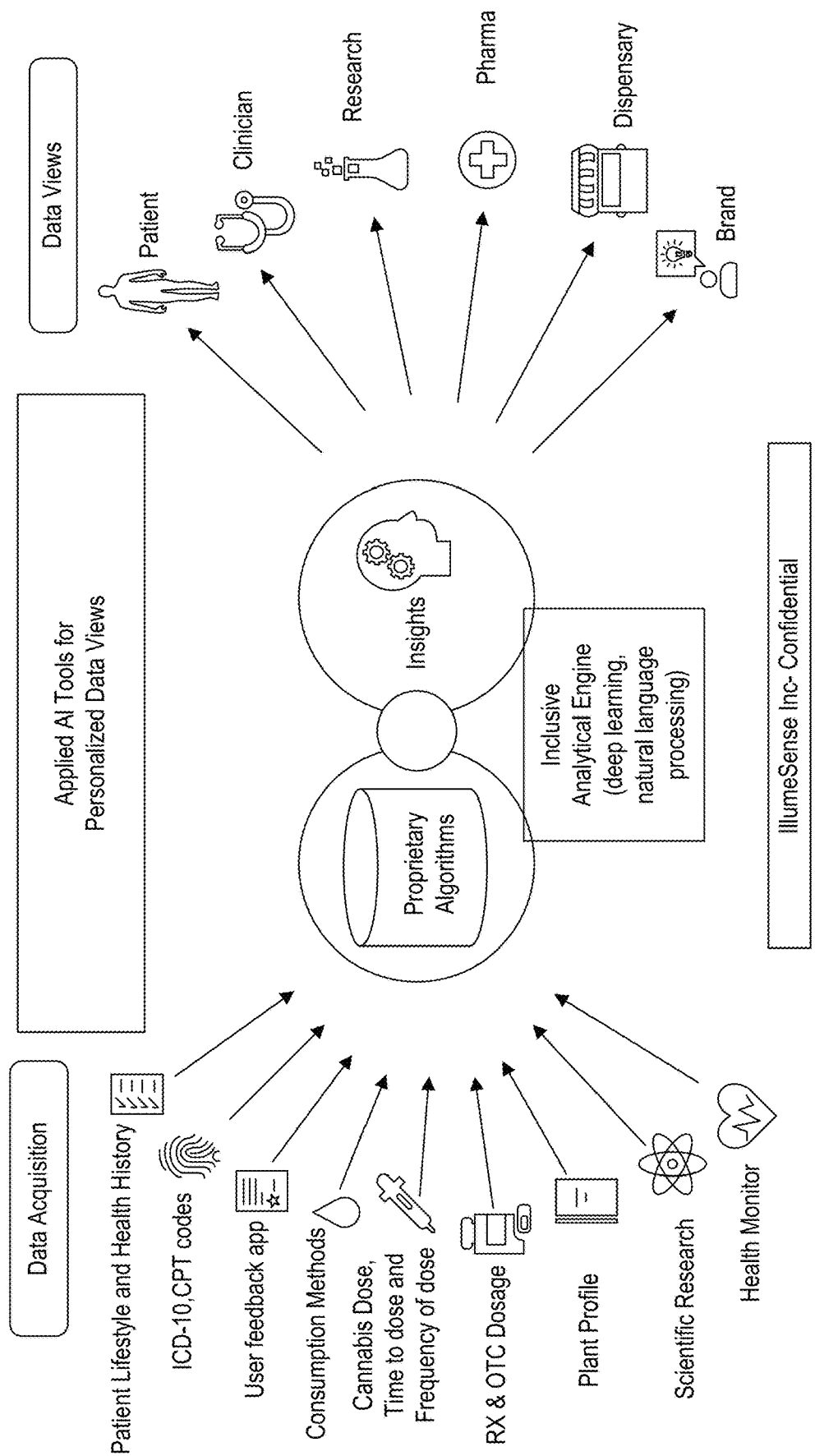
FIG. 2 illustrates personalized data view for the wellness system.

The data stored in the DB 108 may be provided as input to a data filtering and synthesis engine 116 that filters the data by selectively discarding some data, and synthesizes data by combining specific sets of data. The principles of the data filtering and synthesis engine 116 is described later with reference to FIG. 3 and FIG. 4. Synthesized data from the data filtering and synthesis engine 116 is provided as training and/or reconfiguration data 109 to a clinical decision support inference engine (CDSIE) 119. The synthesized data is also provided to the monitoring inference engine 104 as training and/or reconfiguration data. In some implementations, the synthesized data is provided to dashboards 110 (e.g., data rendered on a display), such as business insights (for dispensaries) dashboards and health effect (for manufacturers) dashboards as part of the respective data viewpoints appropriate to corresponding dashboards. FIG. 2 illustrates on the right-hand-side a set of exemplary viewpoints.

The clinical decision support inference engine 119 (CDSIE) infers the most effective regimen/prescriptions for specific patient conditions. The output of the clinical decision support engine 119 may also be made available to the clinician/educator 107 as a resource, for example providing recommendations, or to another machine that may be at least partly responsible for making clinical decisions. Further, population research data 111 may be made available to the clinician/educator 107, such as through the DB 108 or in some other manner. This data exchange is depicted by the incoming arrow 114 into the clinician/educator 107. In some implementations, the research data 111 may also include data from virtual clinician rounds. The virtual clinician rounds, based upon simulated and/or actual patients and patient conditions, may be used to obtain feedback from the clinician/educator 107 that is then added to the database for additional robustness. For example, this may provide objective insights as observed by clinicians/educators. Further, the virtual clinician rounds may be based upon the clinician/educator 107 being at a remote location from the patient. The data filtering and synthesis engine 116 preferably has access to all the data in the DB 108 and selectively pre-processes the data and synthesizes specific data to provide to the monitoring inference engine 104 and CDSIE 119 as training and/or reconfiguration data and also to provide input data to various customized dashboards. The different dashboards may be different from one another, with some dashboards including a first set of data, with other dashboards including a second set of data, where some dashboards exclude some of the data shown by other dashboards.

The patient's 106 inferred data may be contributed to the research data 111 as indicated by the incoming arrow 112 into the research data 111 from the DB 108. CDSIE 119 may have additional capabilities to rank products based on their efficacy and/or patient testimonials. In yet other implementations, patient's traditional prescription information, patient OTC medication/prescription data 115, is also made available to the clinician/educator 107, and added to the set of data stored in the DB 108. It is also available to the monitoring inference engine 104 as desired, for example, to be aware of any changes in the OTC medication/prescription data 115 of the patient 106.

Figure 3:
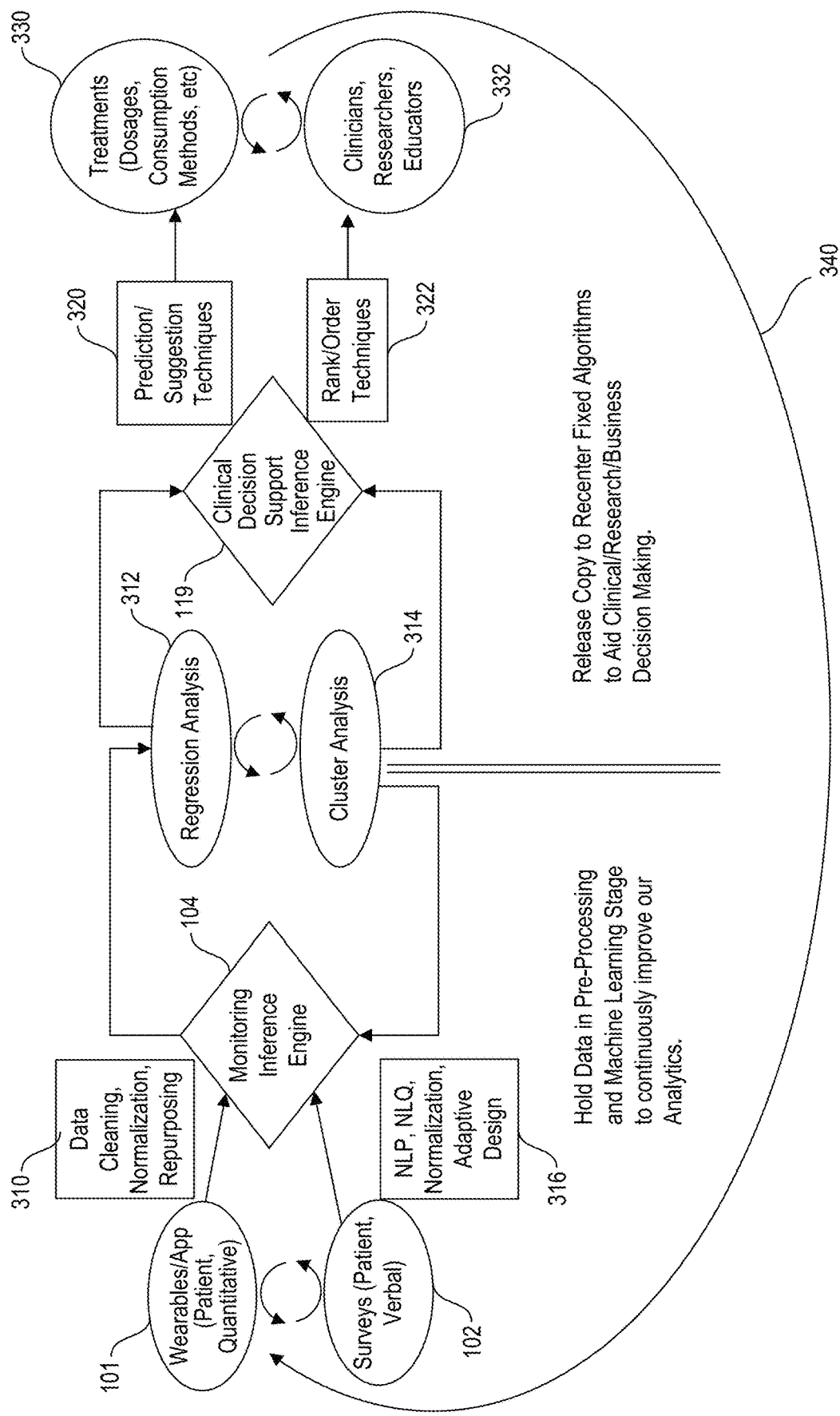
FIG. 3 illustrates an interaction pattern between a monitoring inference engine and a clinical decision support engine of the wellness system.

Referring to FIG. 3, an exemplary interaction between the monitoring inference engine 104 and the CDSIE 119 is illustrated. The interaction between the engines is cyclical, with the CDSIE 119 updating its data at a temporally slower rate than the monitoring inference engine 104. With reference to the monitoring inference engine 104, raw data is collected from wearables and other autonomous data sources 101 and user (e.g., patient) input data 102 (e.g., surveys and verbal information) on a website or other input mechanism. The user input data 102 may be voice data that is then interpreted or analyzed. The user input data 102 may be natural written language or otherwise notes that is then interpreted. The user input data 102 may further be modified by a natural language processing in the case of spoken inputs, natural language querying, normalization, and adaptative design 316. The received data may be cleaned and normalized 310 by a variety of techniques according to its type (e.g., quantitative or verbal) prior to being provided to the monitoring inference engine 104. The monitoring inference engine 104 tracks the data points over time, structured logically, and displayed on customized dashboards according to the patient's needs. Machine learning tools, which are also referred to elsewhere in part as the data filtering and synthesis engine 116 (FaSE), are then applied to determine the preferred classifications and classification boundaries for the data structures as additional data is provided, which may change as a result. The classifications and boundaries may be determined, for example, by a regression analysis 312 and a cluster analysis 314. The monitoring inference engine 104 may receive the results of the regression analysis 312 and cluster analysis 314 for further processing. The regression analysis 312 may be temporal in nature and/or in different time scales, and temporal nature and/or different time scales of the data being used may vary based upon the patient, and temporal nature and/or different time scales of the type of data being used, and/or temporal nature and/or different time scales of the characteristics of the data being used. The output of the monitoring inference engine 104 is provided to the clinical decision support inference engine 119 (CDSIE), which updates the technique for ranking the importance of datasets and predicting effective updates to treatment parameters. These updates may undergo human consideration and editing, and are then fed back to the beginning of the process as the new data and containing structures provided by the initial collection process. In general, the clinical decision support inference engine 119 (CDSIE) may change the boundaries of the clusters, as desired.

The clinical decision support inference engine 119 may include prediction and recommendation techniques 320 for treatments 330 (e.g., dosages, consumption, methods, etc.). Such prediction and recommendation techniques for treatments may, in part, take the form of a new CPT (Current Procedural Terminology) description with which a new CPT code may be associated because the new CPT description may include the cannabis treatment services and procedures in addition to (and in combination with) traditional medical services and procedures (expressed by existing or traditional CPT codes), plus possibly digital prescriptions/treatments and services as well. Such an augmented CPT description may include the parameters of the specific Cannabis procedure, cannabis therapy services, or cannabis therapy such as cannabis dosages, consumption methods and frequency, in addition to patient's traditional prescription and over-the-counter medication which may be expressed e.g., in terms of NDC (National Drug Code) codes. Such augmented CPT descriptions may be associated with traditional ICD (International Statistical Classification of Diseases and Related Health Problems) codes for conditions such as e.g., migraines, insomnia, anxiety, inflammation, or chronic diseases such as cancers. The clinical decision support inference engine 119 may also include rank/order techniques 322 for ranking the importance of datasets and predicting effective updates to treatment parameters that is provided to clinicians, educators, and researchers 332. The data from the clinical decision support inference engine 119 is provided back 340 to the monitoring inference engine 104 for subsequent processing.

Upon a pass through the system 340 from the clinical decision support engine (CDSIE) 119 back to the monitoring inference engine (MIE) 104, in addition to making intended inferences according to a given use case (vector between variables monitored and variables included in decision support case), the system may also track noteworthy changes in secondary variables which are tracked. The accumulation of such secondary changes detected by the MIE 104 may reach a threshold at which their sum computed from the current state in the MIE 104 equals an existing vector (var1, var2, var3, . . . ) in the CDSIE 119. For example, a subset of secondary symptoms tracked over time may eventually reach a state at which it equals a condition as that condition is currently represented by a vector (of symptoms) in the global system, requiring a persistent alteration to the MIE 104. In the event of a non-trivial involvement of diagnostic or treatment modalities from outside traditional medicine in 320, this vector between secondary variables may provide evidence in support of introducing new ICD-10 codes or formally defining new relations between them and other codes.

The process depicted in FIG. 3, may be considered as follows. At any given point in time, the process has "raw" (e.g., new) data coming in, processed data running through models, model_results_shaping techniques, and techniques providing repurposed/"new" data. The process consistently serves two purposes. The first purpose is to continuously run machine learning models and optimize data classifications, boundaries, and processing techniques in an efficient manner with respect to both domain (e.g., healthcare) specific concerns and computational efficiency. The second is to provide users with a consistent, readily understandable, and ontologically stable medium for interacting with the most recently delivered stable data.

Given the rapidly evolving body of information available in the cannabis space (e.g., decades of anecdotal data, but only recent accumulation of clinical/scientific data), it is desirable that the system includes a highly scalable and adaptable inference model which reacts to broad influences such as real world events necessitating automatic change of hyperparameters, change of activation functions, reshaping of core data structures, or other major systemic changes. At a fundamental level, the process has classes of data points whose values span the range defined by the boundaries of each class. The process may, for example, ask two questions of a data point or collection of related points. The first question may be "to which category does this data point belong?" The second question may be "are these categories of data divided up into the most informative units for our purpose?" In this way, the three engines interact because the way the data is monitored influences the efficacy of decision making, and the way new decisions are made influences the efficacy of established monitoring techniques. As a result, the system uses relevant data to make decisions, and the system makes decisions that lead to more relevant data.

Figure 4:
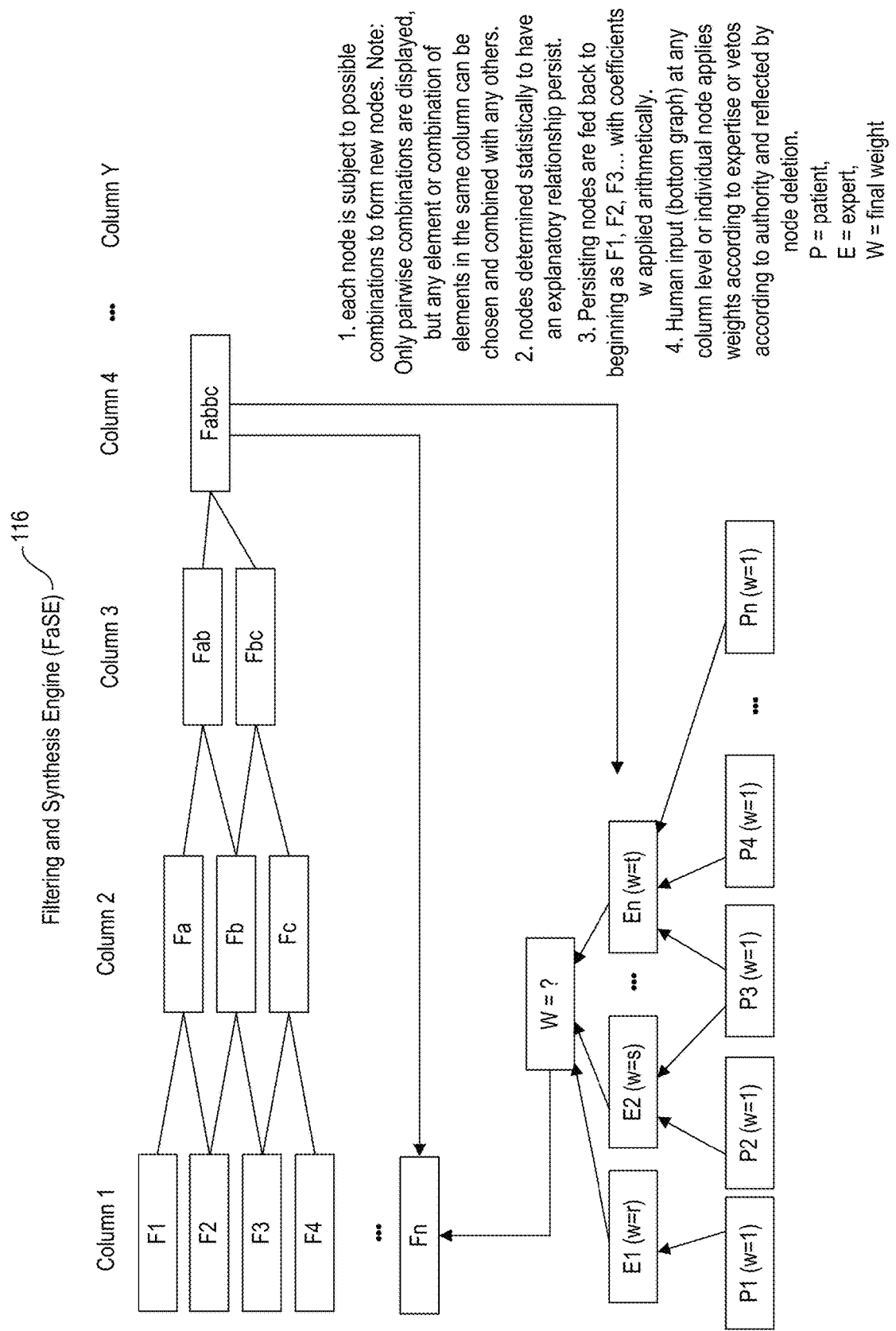
FIG. 4 illustrates a data filtering and synthesis engine for the wellness system.

Referring to FIG. 4, the illustrated process operates continuously on the left side (101, 102, 104, 310, 312, 314, 316) of FIG. 3, and more stable periodic copies are released to the right side (119, 312, 314, 320, 322, 330, 332) of FIG. 3. The process depicted in FIG. 4 is a further detailed explanation of what is happening to the data in the center (312, 314) of FIG. 3. FIG. 4 shows the manner in which the data is recombined in preprocessing after the most recent full iteration of FIG. 3 provides new information about the relevance of previously tested combinations of data points. The following may be observed from the pattern outlined by the rectangular arrows on the left and right halves of FIG. 3: First, the left side is cyclical, where data continues to come in from collection methods, and the data goes into the model, either fitting into the current model or showing evidence that the current set of clusters is insufficiently descriptive and thus in need of revision. Second, the right side of the model is unidirectional, where it is desirable to provide a generally stable user experience, so updates to the CDSIE (FIG. 1 119) occur periodically rather than continuously, i.e. the most recent set of "persisting" (e.g., having a strong explanatory relationship and thus being kept) nodes collected from the process in FIG. 4 determines the structure of the techniques reflecting the details of the right side of FIG. 3. The persisting nodes may be F1, F2, F3, F4 . . . Fn, Fa, Fc, Fbc, Fabbc. The weak explanatory relationship nodes Fb and Fab may be the remaining nodes.

Referring to FIG. 4, the process may be illustrated as follows. The system starts with several sets of data about a population of patients collected in the manner illustrated in FIG. 1 through FIG. 3 (see FIG. 4, column 1). Thereafter, the system may determine possible combinations of types of data points (for N types of data points, combinations of 2, then 3, then ..., then N of those types of data points). The system may run a regression analysis 312 on each of these combinations, determining which have a strong explanatory relationship (FIG. 4, columns 2 to N). Those combinations that have a strong explanatory relationship (may be indicated by high R^A2 (R-Squared) value or other suitable measure) are maintained and those that do not have a strong explanatory relationship are set aside (e.g., example of data limiting procedure). Just like the system need not further consider these generally unrelated combinations of data points, the system need not consider the original isolated data points that persistently coexist with N others in explanatory contexts. At the end of an iteration (generally referred to as iteration i), the system is left with different sized combinations of data points which are bound together in statistically significant explanatory contexts. The resulting combinations are then treated as the individual data points in iteration i+1.

In general, a high R^A2 value (close to 1) or other favorable measure, means that the current model successfully explains variation in the real data. For a factor receiving a high R^A2 value or other favorable measure to "persist", means that it is deemed relevant as a unit to consider in future cannabis healthcare transactions. Since the system may want the model to automatically point stakeholders to the best of initial considerations when approaching a health concern with a cannabis solution, it is desirable that the engine (middle portion of FIG. 3) to cluster related data points to keep the fixed techniques optimized.

The data filtering and synthesis engine 116 attempts to improve upon the collection and consideration of relevant data points. In a clinical or business decision making context in the cannabis space, the system may find at the individual or small group level that one size does not fit all, as in the data currently collected and the techniques of gleaning insight from that data are not the most effective and/or not the most efficient means for approaching a particular problem with a cannabis aided solution. By repeatedly improving the training data through this process of recombining and statistically evaluating the data 314, the system may ultimately improve both the relevance of the data collected and the accuracy/efficiency of clinical decision making by positioning users uniquely ahead of repetitive, one size fits all treatment. The system incrementally moves past traditional one case at a time memorization of effective treatments.

The data filtering and synthesis engine 116 may collect data points and training data is prepared through computing a substantial number of possible combinations of data points, and running them through regression models 312 to test for explanatory relationships. These tests may yield the following six cases or others on an individual iteration (e.g., column n to column n+1): 1. relevant+relevant=relevant; 2. relevant+relevant=irrelevant; 3. relevant+irrelevant=relevant; 4. relevant+irrelevant=irrelevant; 5. irrelevant+irrelevant=irrelevant; 6. irrelevant+irrelevant=relevant.

The system may start with the data units and structures as dictated by traditional western medicine or current cannabis healthcare practices, and incrementally proceed toward determining which units and structures are relevant for particular types of patients and treatments observed in the cannabis space by other particular stakeholders. In general, each stakeholder (e.g., what a patient may want to know about similar patients, versus what a clinician may want to know about an individual patient over time, versus what a business interest may want to know about a particular population of potential clients among the wellness users) may be different. Each iteration i, serves as the collected training data for the next iteration (i+1) of the model in FIG. 3, as well periodically, the reconfiguration of user dashboards (shown in FIG. 1). To clarify, what may be combinations in iteration i, if determined to have an explanatory relationship, are then units in iteration i+1. According to limits on class size imposed on the data, and the results of regression models 312, clusters of data may be split into multiple clusters or eliminated (e.g., temporarily or entirely) in order to improve the cluster analysis portion 314 of the model, referred to in FIG. 3. The nodes at the bottom portion of FIG. 3 reflect an additive process of patient data accumulation (P(n)), a multiplicative process according to expert opinion (E(n)) and a final weighting w that accounts for all of these in linear combination. This may be applied at any time it is determined to be mathematically significant (e.g., weight !=1) and/or structurally significant.

By way of example, possible nodes in layer 1, may include, diabetes, family history of heart disease, ketogenic diet based choices logged in app, preferred consumption method=smoking, cannabis dosage=2 joints/day, Rx=aspirin 250 mg/day, health data=avg heart rate 60 bpm. It is noted that these examples are single instances of data points that would fit into the categories on the left side of FIG. 2.

By way of example, possible nodes in layers 2 to n: layer 2 (2 data points each): (consumption method & cannabis dosage=smoking, 2 g/day), (Rx dosage & cannabis dosage)=aspiring 250 mg/day, cannabis; Layer 3: (3 data points) (ICD-10 code=cancer diagnosis, consumption method=smoking, cannabis dosage=1 g/day).

It is noted that the nodes may also be the result of anecdotal data points from right side after the processing of natural language data or digital signals (e.g., voice data).

The particular technique preferably includes three separate, either physically or logically, components that achieve limiting, privileging, and re-leveling of included data. Patients provide individual, single counted data which is generally limiting data. Clinicians, researchers, and other experts provide privileged data according to their reputation and/or medical specialty (e.g., cardiology) which weights the aggregated factor (a*b*c* . . . ) which is generally privileging data. For example, depending on the reputation of the clinicians, researchers, and other experts their data may be weighted with respect to domain specificity, accumulated rank, or other relationships placing them among other such clinicians, researchers, and other experts. Further, a condition indicated by a patient may trigger the selection of a particular clinician/educator, such as neuropathy pain patient may be directed to a clinician with expertise in pain management, or a patient with anxiety as their primary condition may be directed to a clinician/educator trained in psychiatry. In this manner, different clinicians, researchers, and other experts will have different influence on the data, depending on their reputation or other factors contributing to their likelihood of providing meaningful data. In addition, the selection of an appropriate clinician/educator increases the likelihood of more effective care with reduced side effects. The analytical engine (FIG. 3) processes data and returns mathematically informed insight to the community of patients and medical experts. If patients indicate that a particular treatment did not work, or clinicians indicate that certain findings violate established knowledge or practice, these can be removed (by veto) from the model or otherwise reduced in influence, thus limiting the dataset going back through. Furthermore, each iteration of the model collects this limited data set from a variety of complexity levels of data, and redefines it as the units to be initially considered. For example, in FIG. 4, Fb and Fab (e.g., weak explanatory relationship nodes) would not be fed back to column 1 of the model and the remaining nodes would be fed back as column 1 which is units, although some of these were previously combinations.

There may be any suitable number of combinations of any N data points. The process aims to define persistent combinations as units. What may initially/traditionally be considered separate data points, may be found by the system to reliably coexist or correlate. This suggests that a more efficient and effective approach is to treat those points as one type of unit for future training and testing data informing the model. The persisting nodes that are more relevant are preferably added to the original list, while others that are less relevant may be deleted according to variably defined confidence interval.

There are two underlying questions that frame the use of cannabis data to efficiently and accurately provide insight to a variety of stakeholders: 1. how is the data collected, processed, and moved through the space of users and inquiries? E.g., who are the users, what do they have, and what do they want? And 2. which data in which frame is relevant to a given issue and reliably provides insight? E.g., is the incoming data really what users need, or are there some basic logical manipulations the user may perform, expending their own temporal, organizational, and cognitive resources before the system has the ingredients to make a decision?

FIG. 3 illustrates a technique used to optimize the answer to question 1. Briefly, the system gathers the data from a variety of sources in a variety of formats, cleans it so that it can be used together effectively, and puts it into the current frame for storing it and representing it effectively to users. But where did this data originally come from? It came from patients and their devices and testimonies that store their data. But where did that come from? That came from storage in devices programmed to collect certain data from the patients, and established approaches (practiced in clinical settings and partly systemized in the clinical decision support inference engine) of medical professionals to eliciting testimony from patients. Analogous situations exist for different groups of stakeholders. With this in mind, the system may be explained from the right side of FIG. 3. In the middle, the system includes machine learning models which are designed to mediate and optimize this exchange of information in two ways. The first way is by determining the spread of data within individual clusters of data. The second way is by determining the units of information that should constitute the clusters themselves. In this way, stakeholders are informed about particular data points in relation to other data points of the same kind, and stakeholders can be assured that the kinds of data points they seek information about are in fact informative in attempting to answer the questions stakeholders hope to answer.

FIG. 4 represents a system used to optimize the technique used to address question 2. The data currently being collected in scientific and clinical contexts is that which has been deemed relevant over years of scientific theory development and clinical practice to validate these theories. These are human driven processes and have long been informed by western scientific and clinical practices in contemporary legal landscapes, which excluded cannabis specific insight and mostly did not benefit from modern machine learning technologies. The process depicted in FIG. 4 remedies this by systematically combining any arbitrary number of relevant data points to structure new independent variables, and tests their reliability in predicting dependent variables. Over time, data points that do not factor into predictions are discarded, and data points that do are kept. Furthermore, combinations of data points divided along current lines, are tested, and effective combinations are fed back into the model as units which do not need to be recombined. In this way, the models and the stakeholders providing data to them and receiving insight from them are operating with the most relevant data and the most effective methods of leveraging it.

Figure 6:
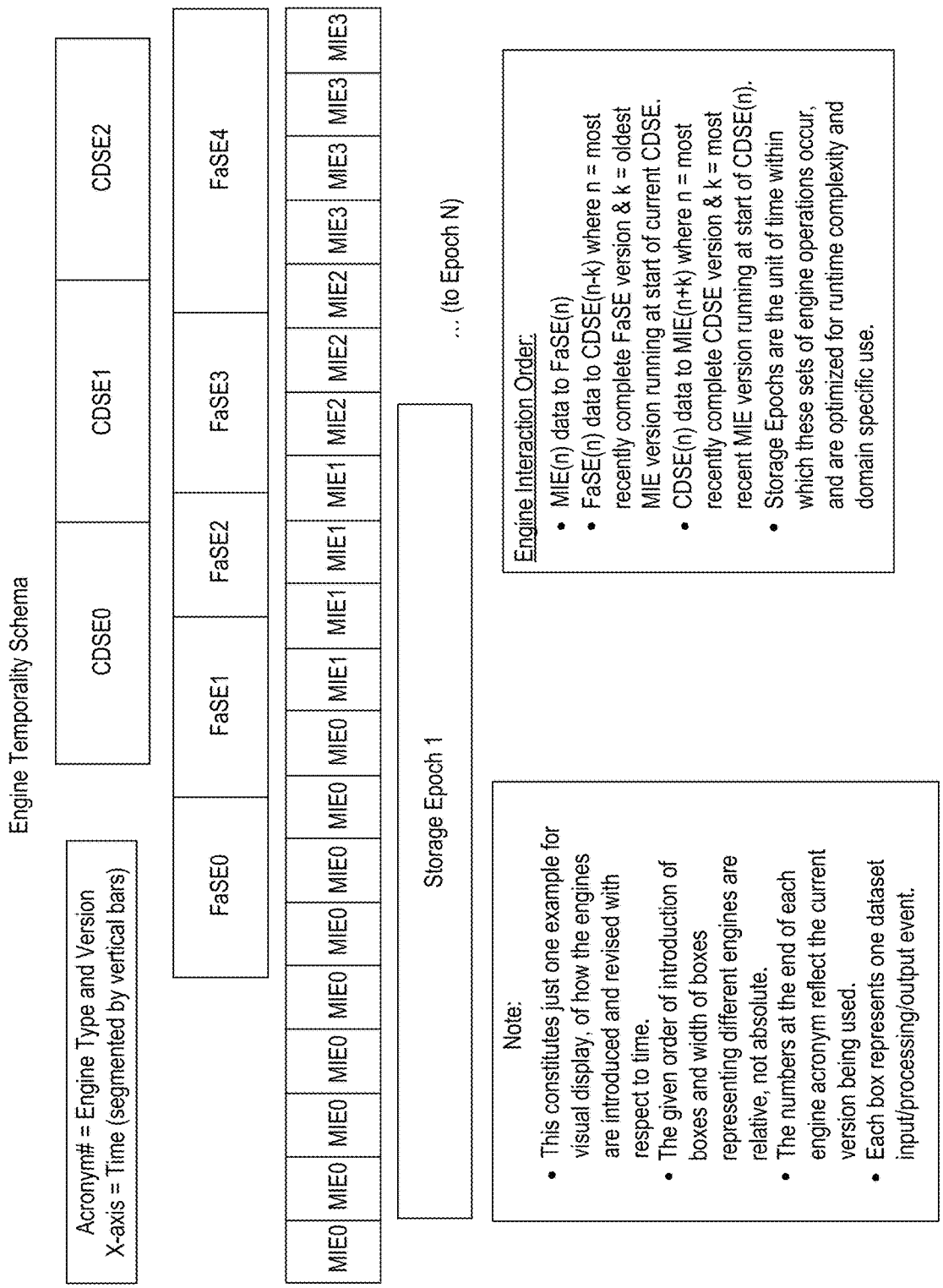
FIG. 6 illustrates an engine temporality schema.

The process as previously described, the interaction of the MIE and the CDSIE over time as in FIG. 6, may be globally influenced in the form of updates to hyperparameters in the machine learning ensemble. The relations between these hyperparameters, and their efficacy at any given time, may be informed by biphasic or multiphasic properties of a corresponding treatment, e.g. changes in efficacy such as the development of tolerance to a given dose, the ebb and flow of physiologically noticeable results, any of which may show multiple phases.

Observations of phasing by the MIE 104 may lead to persistent alterations of the CDSIE 119 including but not limited to phase dependent changes to parameters or hyperparameters in the Filtering and Synthesis Engine 312, 314. It may also lead to changes in choice of activation function or other architectural features of the ensemble that may leverage prior knowledge of phasing tendencies.

The process illustrated in FIG. 3, fits in logically after steps pointing to the database 108, and before the database 108 itself. Information that users provide via the web, wearable device, and app interfaces (or otherwise) goes into the database driving those interfaces, and a copy goes into the database hosting the machine learning pipelines. The create, read, update, and delete (CRUD) process applied to the latter database is determined by the analytical results (after the left side of FIG. 3, before the CDSIE), which will alter the database so that it hosts the data that goes into preprocessing for the next iteration of the engine. The current best set of inferences at any point may be applied to further optimizing the CDSIE itself, which is governed by the same database that hosts what users see on the website and/or the app (or otherwise).

Figure 5:
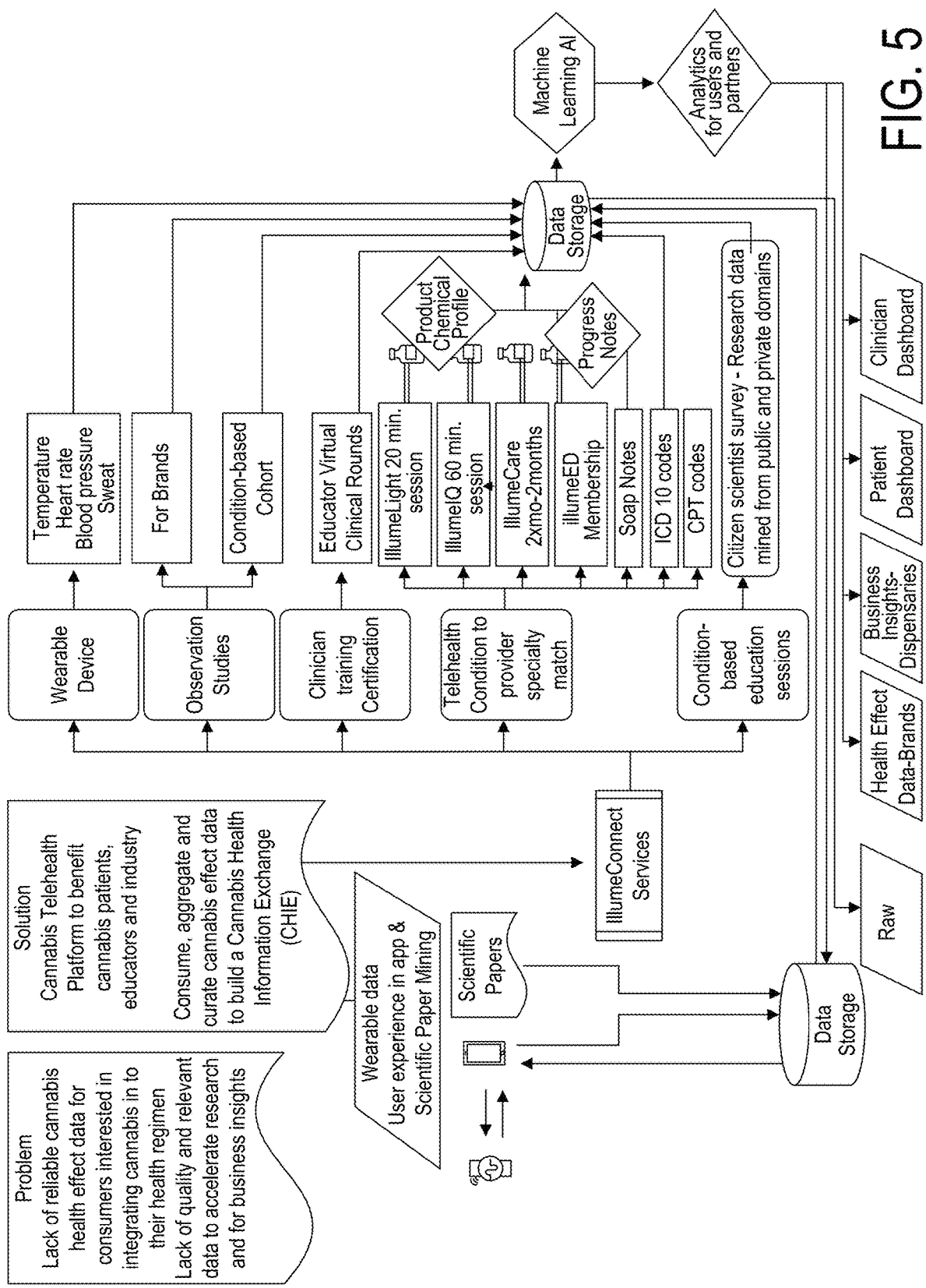
FIG. 5 illustrates an embodiment of another portion of the wellness system.

The process depicted in FIG. 4 illustrates a content independent analytical procedure that filters data to be included in the next iteration of the model explained in FIG. 3. The process depicted in FIG. 4 logically fits between the two nodes marked "Data Storage" in FIG. 5. FIG. 3 and FIG. 4 depict the details of the two rightmost nodes in FIG. 5, "Machine Learning/AI" and "Analytics for users and partners". The machine learning/artificial intelligence portion (left side of FIG. 3) operates continuously, and the results are periodically released to restructure "analytics for users and partners".

In the form of a data insights dashboard, the dashboards may not render certain unrelated information for particular audiences and render such certain information for others based upon the particular viewers. For example, a patient dashboard may include product, dosing, frequency, and timing information relevant to a reduction in pain. The clinician/educator dashboard may include chemical profile of the cannabis for a particular condition and secondary condition relief. It may also provide insights into how often they accurately treated a particular condition and the clinician/educator may learn from such information for future patients with similar conditions. An industry dashboard may have data about the condition for the product selected together with demographic information of the patients with positive and/or negative outcomes for the purposes of marketing. Various brands may also have a research dash board if they have participated in observational studies with cohort of patients with a particular condition using a particular chemical profile of the cannabis.

In general, the monitoring inference engine 104 is stable while categorizing incoming data and updating displays according to the current data structures in the monitoring inference engine 104. In general, the monitoring inference engine 104 is unstable (e.g., in a stage of reconfiguration or retraining) when receiving new category boundaries from the CDSIE according to iterations of regression analysis, updated categories according to cluster analysis, and additional human insights.

In general, the clinical decision support inference engine 119 is stable when running existing techniques in the clinical decision support inference engine to aid clinical decisions. In general, the clinical decision support inference engine 119 is unstable when receiving data packaged as updated data structures from the monitoring inference engine 104 and updated techniques to account for them.

Referring to FIG. 6, the different engines may have different temporality with respect to their data processing. By way of reference, M=memory capacity, Cf=FaSE complexity, Cc=CDSIE complexity, T=time, i=iteration, n=iteration number, and E=storage epoch. The numbers at the end of each engine acronym reflects the current version being used. Each box represents one dataset going through one input/processing/output event.

The monitoring inference engine 104 may include the following:
  Start Condition: patient or clinician enters data;
  Update Condition: 1.CDSIE memory capacity (M) or 2. FaSE complexity (Cf) limit or 3. end of time period (T) reached;
  Input—1. data from wearables, data entered by patients/clinicians (i=n) 2. data entered from CDSIE (i=n−1);
  Processing—data cleaning;
  Output—1. training data for FaSE (i=n+1) 2. data for dashboards (i=n).

The filtering and synthesis engine (FaSE) 116 may include the following:
  Start Condition: 1. MIE memory capacity (M) or end of time period (T) reached;
  Update Condition: updates every time it runs;
  Input—data sets: 1. MIE (i=n), 2. FaSE (i=n−1);
  Processing—regression analysis+cluster analysis, arithmetical recombination of data;
  Output—1.new structures (boundaries/clusters) for FaSE, MIE, and CDSIE 2. recombined data (to populate CDSIE).

The clinical decision support inference engine (CDSIE) 119 may include the following:
  Start Condition: clinician seeks decision support or enters data;
  Update Condition: 1. (FaSE complexity (Cf)/CDSIE output complexity (Cc))>K (constant);
  Input—1. structures from FaSE 2. recombined data from FaSE 3. data entered by P/C;
  Processing—1. run through decision algorithms 2. match to existing structures;
  Output—1. calculated decision retrieved from database 2. new data points for MIE.

The length of time for which data is stored, called the "storage epoch" (E) may be optimized for reducing runtime complexity according to the historical pace of the flow of data through the system. In the long term, the system may optimize memory (M) so that complex medical insight can be stored in the system. In the short term, given the clinical use case, the system may optimize processing power over time reflected by (T) in order to give the best insight to users most efficiently. The individual variables involved in this calculation (M, Cf, Cc, and T) are explained above.

The components of each pattern of execution may also include each of the following: 1. set of given points/investigative choices/independent variables 2. set of desired points/answer format desired/dependent variables/units, 3. Time (T for time elapsed or P for periodic time), 4. Weight (W), which consists of a. Trav1—how many times has the current/parent path been traversed b. Trav2—how many times have all of the subsequent/child paths been traversed (sum of all traversals of different child paths).

The execution pattern referred to above has at least 3 time values that must agree in order to frame one complete iteration, thus the solution set is LCM(x,y,z) where x, y, and z are the return times of the MIE, FaSE, and CDSIE respectively.

In addition to the natural pattern of execution of each engine as in FIG. 6 according to the flow of data, the system may also react to real world healthcare industry updates such as the introduction of new codes by altering the frequency or duration of subsequent executions, in effect "accelerating" (positively or negatively) certain local paths in the system corresponding to human/institutional responses. In reverse, the system may also provide structural evidence in support of such changes to existing logic used to place new healthcare innovations into the preexisting system.

Core changes to the machine learning ensemble and/or data warehousing techniques may be reflected as combinations of one or more of the following path alterations: 1. path from MIE 104 through FaSE 312/314, 2. path from MIE 104 through CDSIE 119, 3. FaSE through MIE, 4. FaSE through CDSIE, 5. CDSIE through FaSE, 6. CDSIE through MIE.

As a result of processing data with the wellness system, the system may identify the particular sensor based devices, such as the wearable devices, for each particular user. Over time, the system may distinguish between the accuracy of each type of wearable device (e.g., such as a result of the FaSE engine), many of which are generally applicable to capture similar data. Based upon this distinguishing, the system may recommend to the user or otherwise a different sensor based device than the one currently being used, or to supplement the data to the one currently being used, to increase the accuracy of the data or otherwise the effectiveness of the system. Furthermore, to the extent permitted by the sensor based device, the wellness system may modify the characteristics of the sensor based device for increased effectiveness. Furthermore, the system may provide cannabis domain specific improvements and feedback to the manufacturers of wearable devices for increased effectiveness.

The flow of data through the system as illustrated in FIG. 3 may depend on the state of two systems: first, the MIE-FaSe-CDSIE ensemble (FIG. 3 and FIG. 4), and second, the Treatment Phasing System (TPS) (FIG. 9). The MIE-FaSE-CDSIE ensemble is triggered when new data is entered into or otherwise made available to the system that can improve the performance and capabilities of machine learning ensemble. The TPS system is triggered when a sufficient number of parallels are detected between user selections of TPS elements.

FIG. 6 illustrates a technique for the management of timing and data flow for the machine learning ensemble. In a similar manner, FIG. 7 illustrates the management of timing and data flow for techniques handling the entry and analysis of user input.

FIG. 7 illustrates a technique for additional optimization of the data architecture to effectively handle structural variety of entries and queries common to different groups of users. The technique illustrated in FIG. 7 may use data and/or information about the timing, and/or complexity, and/or scale of its own past iterations, which may be taken into account in combination with data and/or information about the timing, and/or complexity, and/or scale of procedures for additional optimization data architecture for machine learning operations.

The technique involves making alterations to the structure of data and/or database systems 108 based on anticipated input/output of classes of structures represented by data cleaning etc. 310, NLP etc. 316, prediction/suggestion techniques 320, and/or rank/order techniques 322.

The systems in FIG. 6 and FIG. 7 may act independently of one another or in concert with one another. Data and information about timing, variety, and other metrics may be used by either system to determine whether to operate with the other.

Each arrow in FIG. 7 represents an exemplary operation of the MIE and/or CDSIE which involves the transformation of a particular dataset from structured to unstructured or vice versa over time. This type of process may optimize the storage of select data points according to statistics on their current importance to the system in labeled or unlabeled context.

FIG. 8 illustrates an exemplary process of the MIE/CDSIE ensemble (312, 314, and inputs) for handling inputs that contain genetic data (from plant, human, etc.) which may already possess its own strict structure.

The process shown in FIG. 8 may be used in the modeling of "entourage effect", in which many:many relationships may be selectively preserved and processed where they wouldn't have been in traditional clinical settings.

The process shown in FIG. 8 may be used in order to determine whether genetic data is relevant to include in future iterations of a particular model or process.

FIG. 9 illustrates a process for determining phasing properties of various aspects of treatment including but not limited to improved dosage, method of consumption, and frequency of administration. The process depicted in FIG. 7 (701-705) determines the timing of automated (or research based) structural changes to fixed techniques (320, 322). The process depicted in FIG. 6 determines the timing of automated (or research based) structural changes to techniques in the machine learning ensemble.

In reference to FIG. 9, "treatment" may refer to any pattern of human-computer interaction involving the movement of data aimed at supporting actions recommended to a patient or population of patients.

When available, genetic data may provide a fundamental organizational principle of a data structure with which it is associated (701). A first way that new data associated with the genetic data enters the platform is by its relationships to the genetic data.

When available, genetic data may provide a layer of the Treatment Phasing System (FIG. 9).

When genetic data does constitute a layer of a data structure, the data may invoke a repeated iteration of the TBAC interaction (FIG. 7) pattern according to the pre-existing structure (from domain specific principles) of genetic data. This iteration may produce a layer from 803-805 with a higher probability, or a different layer with lower probability.

The first layer of the TBAC Interaction Pattern (FIG. 7) is preferably considered structured. When available, genetic data determines the structure of generation 1 of the TBAC interaction pattern (701).

Inputs of the TBAC interaction pattern may adhere to the following:
 (1) The length of a UP or SP depends upon the state of the system represented in FIG. 3 with respect to original members of the dataset from UP(n) or SP(n) for the lowest value of n still contributing at least one data point, i.e. length=time until 0 datapoints from either set UP(n) or SP(n) are in processing.
 (2) The system may define a subsequence as any part of the sequence from position x1 to x2 such that (x1>=1 & x2<n) or (x1>1 & x2<n).
 (3) The sequence may start with one or more structured phases (SP).
 (4) Each subsequence also preferably starts with one or more structured phases.
 (5) Each subsequence preferably ends with exactly 1 unstructured phase (UP).
 (6) The data can pass through the UP(n) and SP(n) cycles by any path including a pattern of n SPs followed by 1 UP. E.g SP1, UP1, SP2, UP2, SP3, SP4, UP3, SP5, UP4.
 (7) The sequence preferably ends with the most recent structured phase SP(n).

Genetic data enters the system preclassified in one of N ways (803-805 depicted) where N is a finite set of highly common associations where a genetic data point is one member.

The "epoch" referred to in FIG. 6 as the unit of time for an iteration of the machine learning ensemble, may be shorter, longer, or the same length as the TBAC interaction pattern's structured and unstructured phases are.

The system depicted in FIG. 9 includes any number of layers Layer 1-Layer N, which are known by the system to be organized LIFO or otherwise for stacked comparison. The system depicted in FIG. 9 stores and uses information about intersections between 1-dimensional to n−1 dimensional structures in the stack of Layers 1-N.

While the wellness system has been described with respect to cannabis, the system may likewise be applied to other medical or medicinal treatments and/or wellness environments, including without limitation herbal medicine.

While the wellness system preferably uses inference engines, they do not necessarily use such an inference engine.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit.

Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A method for integrating data for a clinical decision comprising:
   (a) receiving first data, comprised of a first set of data points, over time that is provided to said system as a result of detecting by a first personal tracking device of a user;
   (b) receiving second data, comprised of a second set of data points, over time that is provided to said system as a result of detecting by a second personal tracking device of said user, where said first personal tracking device is different than said second personal tracking device;
   (c) fusing said received first and second data, said fusing comprising leveraging redundancies in said received first and second data to improve accuracy of subsequent analysis;
   (d) identifying changes in said fused first and second data over time;
   (e) inferring from said changes in said fused first and second data, changes in said user's behavior patterns;
   (f) determining, over time and by use of a data filtering and synthesis engine, which of said first and second data and which data points therein explain or appear to explain said changes in said user's behavior patterns; and
   (g) providing, based at least in part on said determining, at least one of predictions, insights, and/or suggestions informing said clinical decision.

2. The method of claim 1 wherein said clinical decision relates to a cannabis treatment.

3. The method of claim 1 wherein said first personal tracking device is a personal wellness device.

4. The method of claim 3 wherein said personal wellness device monitors a sleep of said user.

5. The method of claim 3 wherein said personal wellness device is a wearable device that includes a sensor that monitors said user.

6. The method of claim 3 wherein said personal wellness device is at least one of an activity tracker, a GPS monitor, a blood pressure monitor, and a heart rate monitor.

7. The method of claim 1 wherein additional data, comprised of additional data points, is received by said system from a software application and said inferring changes in said user's wellness is further based upon said additional data, said fusing includes said additional data along with said first and second data, and said determining further determines which of said additional data and data points therein explain or appear to explain changes in said first and second and additional data.

8. The method of claim 1 wherein additional data, comprised of additional data points, is received by said system by an external device embedded in an environment proximate to said user and said inferring changes in said user's wellness is further based upon said additional data, said fusing includes said additional data along with said first and second data, and said determining further determines which of said additional data and data points therein explain or appear to explain changes in said first and second and additional data.

9. The method of claim 1 wherein additional observational data, comprised of additional observational data points, is received by said system and said inferring changes in said user's wellness is further based upon said additional data, said fusing includes said additional data along with said first and second data, and said determining further determines which of said additional data and data points therein explain or appear to explain changes in said first and second and additional data.

10. The method of claim 9 wherein said additional observational data includes data obtained by at least one of a survey, a manual user input, and a soft sensor.

11. The method of claim 9 wherein said additional observational data includes at least one of a pitch and a volume of said user's voice.

12. The method of claim 1 wherein additional prescription data, comprised of additional prescription data points, is received by said system and said inferring changes in said user's wellness is further based upon said additional prescription data, said fusing includes said additional prescription data along with said first and second data, and said determining further determines which of said additional prescription data and data points therein explain or appear to explain changes in said first and second and additional data.

13. The method of claim 12 wherein said additional prescription data includes a description of a cannabis product.

14. The method of claim 12 wherein said additional prescription data includes at least one of a dosage, a timing, a frequency, and a form of delivery of a cannabis product.

15. The method of claim 12 wherein said additional prescription data includes a description of a medical classification.

* * * * *